United States Patent [19]

Kojima et al.

[11] Patent Number: 5,053,499
[45] Date of Patent: Oct. 1, 1991

[54] 2',3'-DIDEOXY PURINE NUCLEOSIDE

[75] Inventors: Eiji Kojima; Hidetoshi Yoshioka, both of Iwakuni; Hidenori Fukinbara, Goutsu; Kunichika Murakami, Iwakuni, all of Japan

[73] Assignee: Sanyo-Kokusaku Pulp Co., Ltd., Tokyo, Japan

[21] Appl. No.: 388,806

[22] Filed: Aug. 3, 1989

[30] Foreign Application Priority Data

Feb. 27, 1989 [JP] Japan ..................... 1-46183

[51] Int. Cl.$^5$ .................... A61K 31/52; A61K 31/70; C07D 473/16; C07D 405/4
[52] U.S. Cl. ........................ 536/24; 536/22; 536/26; 435/88; 435/847; 435/849; 435/852
[58] Field of Search .............. 435/88, 89, 847, 849, 435/852; 536/22, 24, 26

[56] References Cited

FOREIGN PATENT DOCUMENTS 206497 12/1986 European Pat. Off. .
285884 10/1988 European Pat. Off. .
286028 10/1988 European Pat. Off. .
286425 10/1988 European Pat. Off. .

OTHER PUBLICATIONS

APP Environ Microbiol 55 (2) 419–24 (1989).
Chemical Pharmaceutical Bull 36 (10) 4153–6 (1988).
Synthesis (9) 670–4 (1988).
Nucleic Acids Symposium Series 20 17 (1988).

Primary Examiner—Herbert J. Lilling
Attorney, Agent, or Firm—Oblon, Spivak, McClelland, Maier & Neustadt

[57] ABSTRACT

2', 3'-Dideoxy purine nucleosides represented by following general formulae [I] and/or [II]

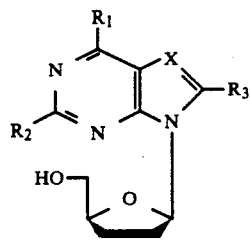

[I]

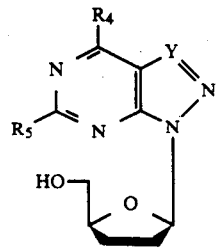

[II]

(wherein X and Y indicate nitrogen atoms or carbon atoms and $R_1$, $R_2$, $R_3$, $R_4$ and $R_5$ indicate each independently any of hydrogen atom, hydroxyl group, amino group, alkyl group, halogen atom, alkoxy group and mercapto group), process for the preparation thereof and applications thereof to the antiviral agent, antiretroviral agent, therapeutic drug and preventive drug for acquired immunodeficiency syndrome (AIDS), and experimental medicine and experimental reagent to be used in genetic engineering are claimed.

1 Claim, 16 Drawing Sheets

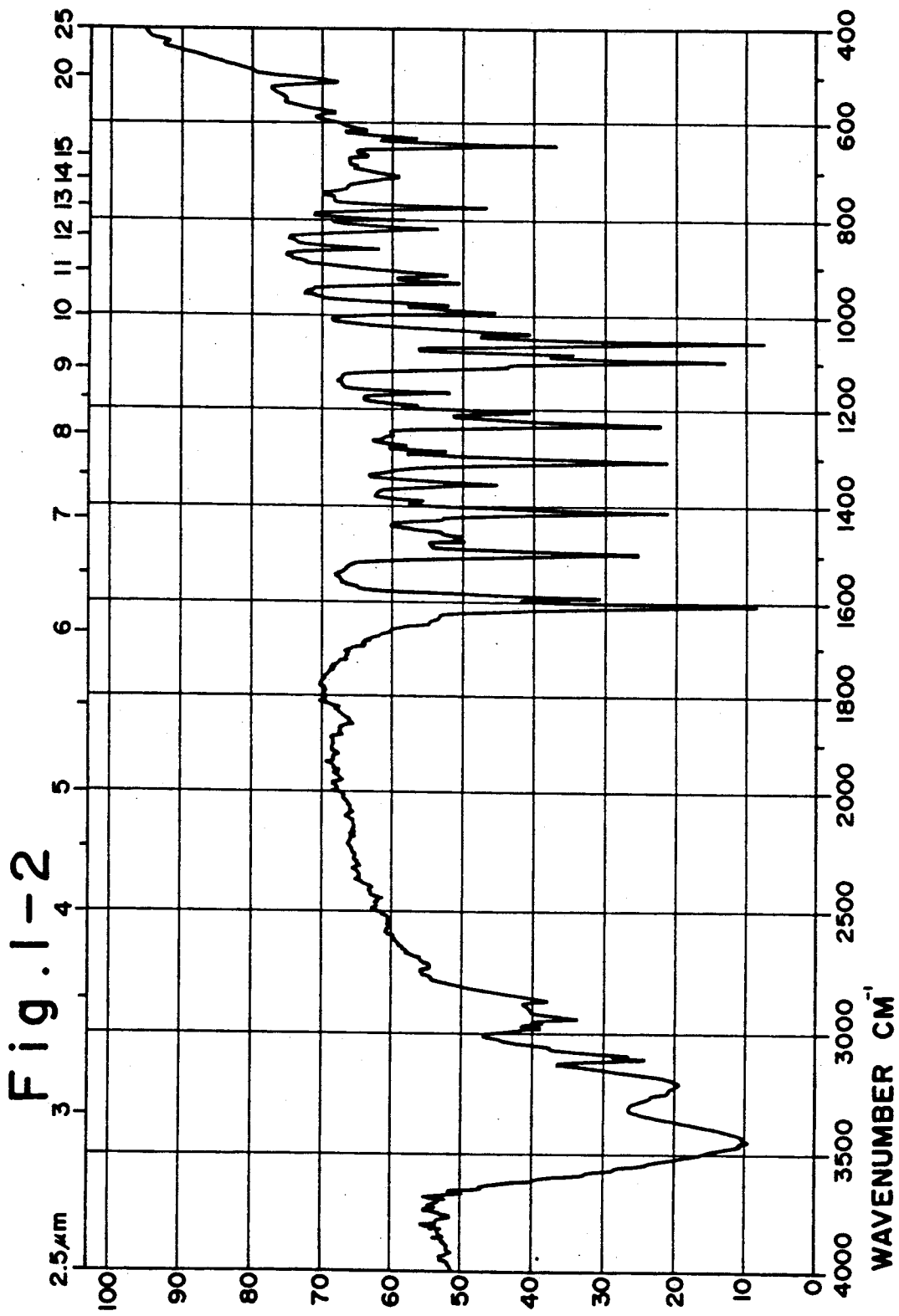

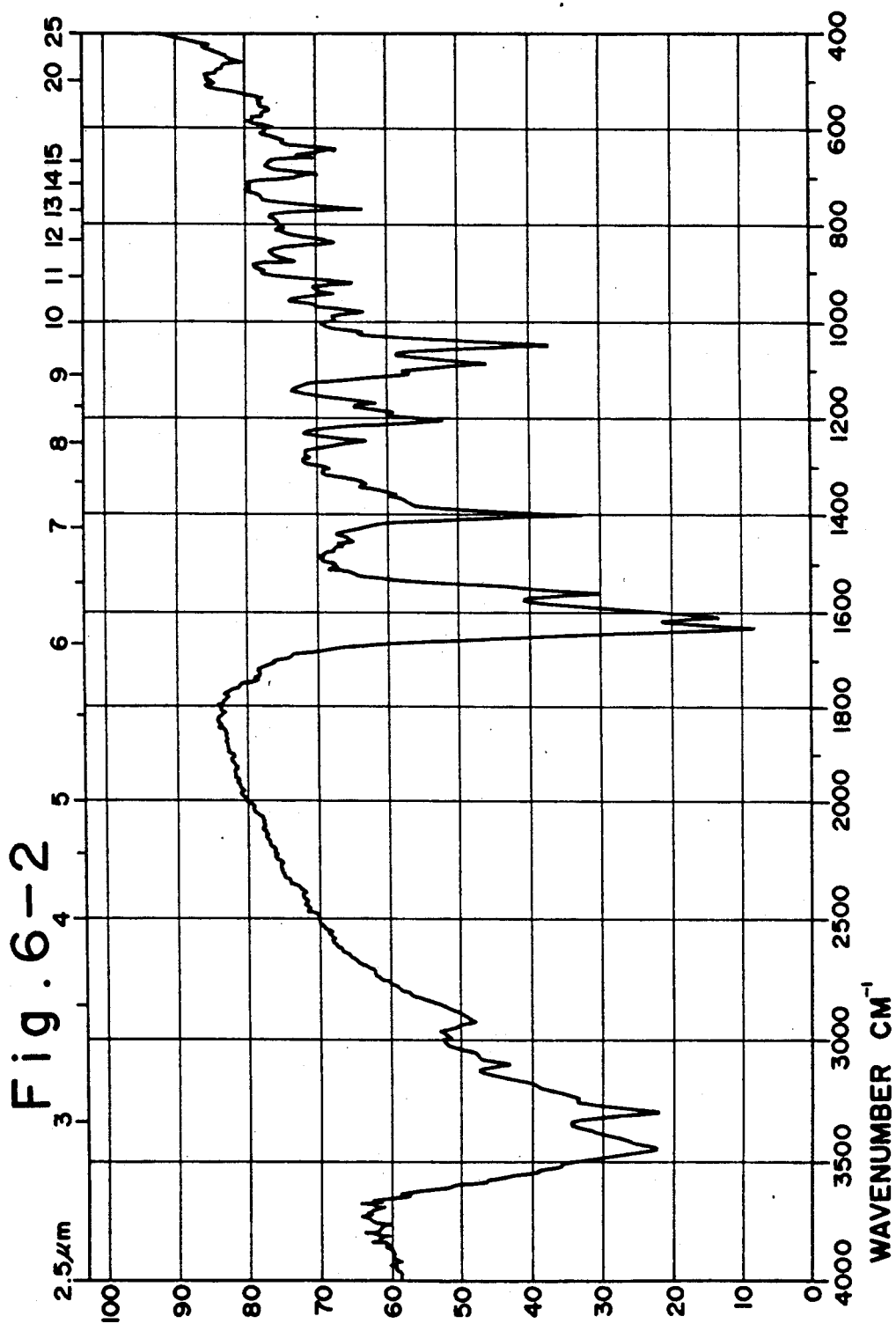

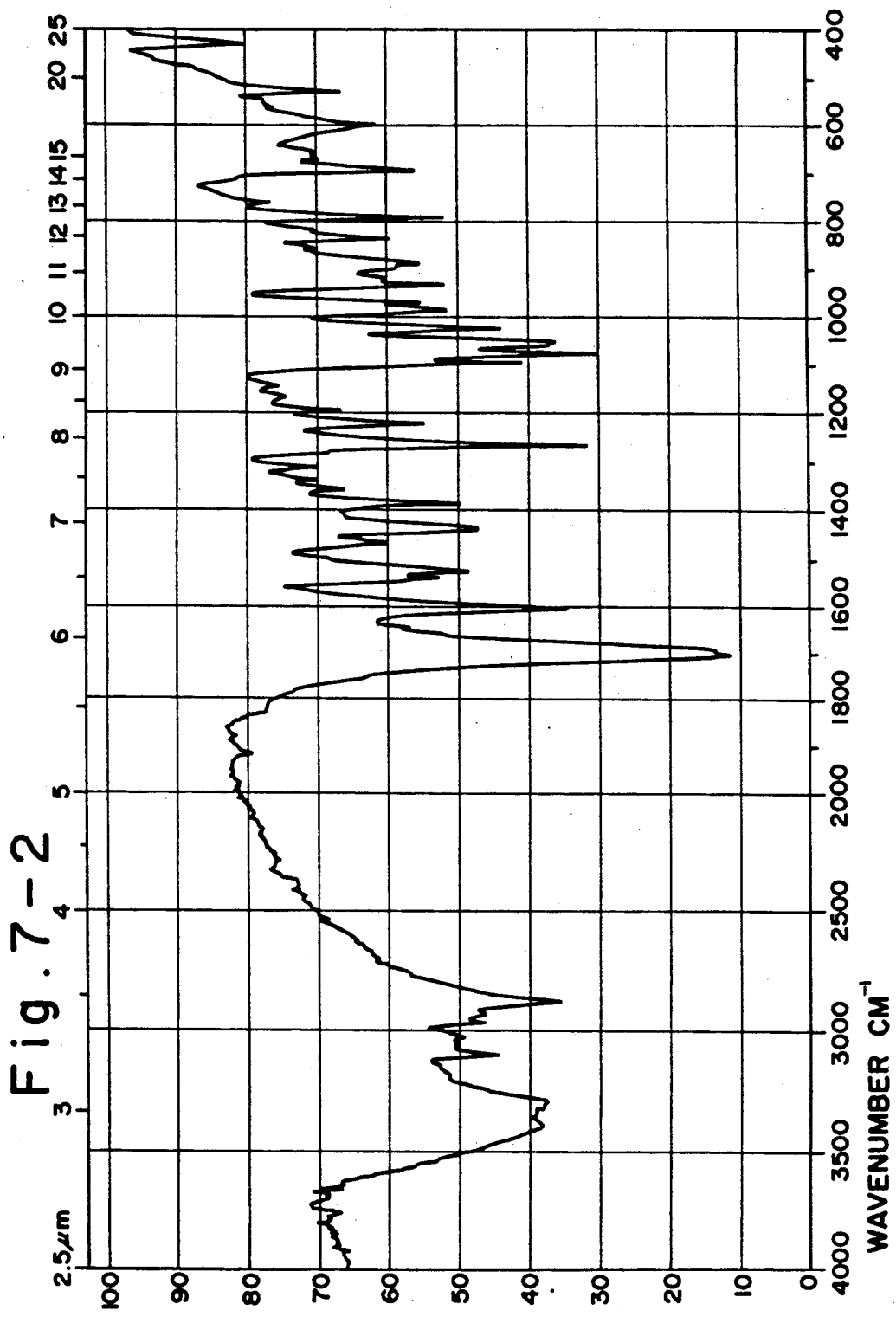

2',3'-DIDEOXY PURINE NUCLEOSIDE

BACKGROUND OF THE INVENTION

The purpose of the present invention lies in novel 2',3'-dideoxy purine nucleosides represented by the general formulae [I] and/or [II] and the processes for the preparation thereof.

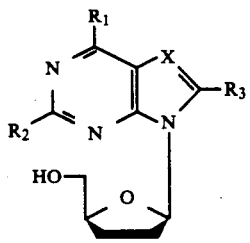

[I]

(wherein X indicates a nitrogen atom or carbon atom, and $R_1$, $R_2$ and $R_3$ indicate each independently any of hydrogen atom, hydroxyl group, amino group, alkyl group, halogen atom, alkoxy group and mercapto group).

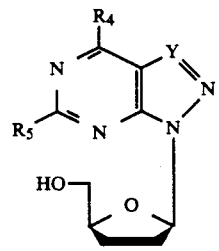

[II]

(wherein Y indicates a nitrogen atom or carbon atom, and $R_4$ and $R_5$ indicate each independently any of hydrogen atom, hydroxyl group, amino group, alkyl group, halogen atom, alkoxy group and mercapto group).

Existing 2',3'-dideoxy nucleosides such as 2',3'-dideoxycytidine (hereinafter referred to as DDC), 2',3'-dideoxyadenosine (hereinafter referred to as DDA) and 2',3'-dideoxyinosine (hereinafter referred to as DDI) have the antiviral property and, because of remarkable effect particularly as antiretroviral agents, they are expected as anti-HIV agents. There are however problems in the aspect of the side effect of said compounds to the human body.

Namely, DDC causes a hindrance to peripheral nerves and DDA and DDI exhibit a toxicity to bone marrows.

Moreover, with 3'-azidethymidine (hereinafter referred to as AZT) being recognized currently as an only therapeutic drug for AIDS, the toxicity to bone marrows is found (N. Engl, J. Med., 316, 557, 1987; idid., 317, 185, 1987; Nature, 325, 773, 1987).

The subject of the invention is to find novel 2',3'-dideoxy nucleosides useful as medicines having the antiviral property, in particular, antiretroviral property by overcoming said problems of known 2',3'-dideoxy nucleosides such as DDC, DDA, DDI, and AZT.

The inventors have synthesized novel 2',3'-dideoxy purine nucleosides by linking 2,3-dideoxyribose to purine bases or purine base analogs modified with various atoms or functional groups (i.e. hydrogen atom, hydroxyl group, amino group, alkyl group, halogen atom, alkoxy group, mercapto group, etc.) through the action of microorganism and have found that the problems of conventionally known 2',3'-dideoxy nucleosides (DDC, DA, DDI, AZT, etc.) aforementioned can be overcome by using these compounds independently or using them together with conventionally known 2',3'-dideoxy nucleosides (DDC, DDA, DDI, AZT, etc.).

SUMMARY OF THE INVENTION

2',3'-Dideoxy purine nucleosides of the invention are those represented by the general formula [I]

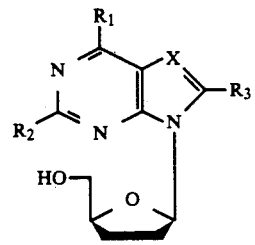

[I]

(wherein X indicates a nitrogen atom or carbon atom, and $R_1$, $R_2$ and $R_3$ indicate each independently any of hydrogen atom, hydroxyl group, amino group, alkyl group, halogen atom, alkoxy group and mercapto group), and those represented by the general formula [II]

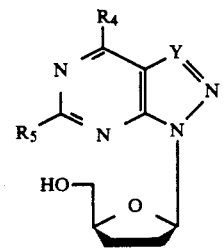

[II]

(wherein Y indicates a nitrogen atom or carbon atom, and $R_4$ and $R_5$ indicate each independently any of hydrogen atom, hydroxyl group, amino group, alkyl group, halogen atom, alkoxy group and mercapto group).

BRIEF DESCRIPTION OF THE DRAWINGS

FIG. 2-1 and FIG. 2-2 show a NMR chart and an IR chart of the compound in Example 6 of the invention.

FIG. 3-1 and FIG. 3-2 show a NMR chart and an IR chart of the compound in Example 8 of the invention.

FIG. 4-1 and FIG. 4-2 show a NMR chart and an IR chart of the compound in Example 10 of the invention.

FIG. 5-1 and FIG. 5-2 show a NMR chart and an IR chart of the compound in Example 11 of the invention.

FIG. 6-1 and FIG. 6-2 show a NMR chart and an IR chart of the compound in Example 14 of the invention.

FIG. 7-1 and FIG. 7-2 show a NMR chart and an IR chart of the compound in Example 16 of the invention.

FIG. 8-1 and FIG. 8-2 show a NMR chart and an IR chart of the compound in Example 18 of the invention.

DETAILED DESCRIPTION OF THE INVENTION

Figure 1:
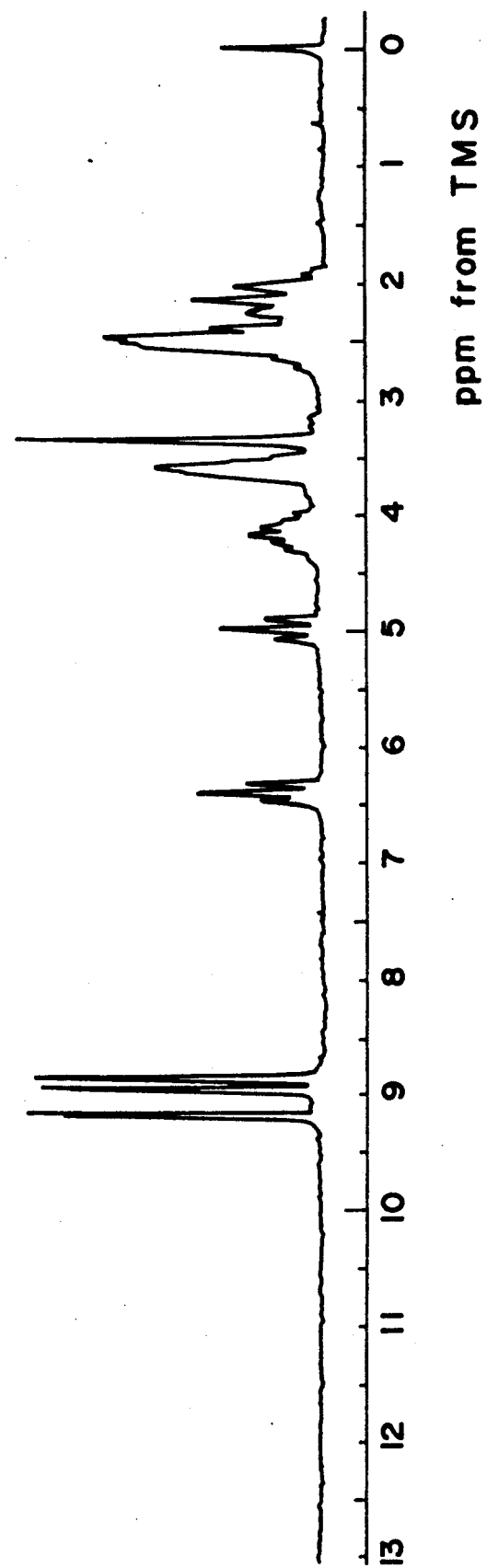
FIG. 1-1 and FIG. 1-2 show a NMR chart and an IR chart of the compound in Example 1 of the invention.

These novel 2',3'-dideoxy purine nucleosides can be synthesized through following process.

Namely, 2′,3′-dideoxy purine nucleosides represented by the general formula [I] can be obtained by allowing purine compounds represented by a general formula [III]

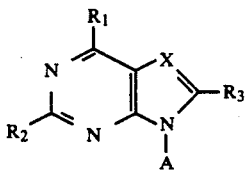

[III]

(wherein A indicates a hydrogen atom, ribofuranosyl group, deoxy-ribofuranosyl group, 5′-phosphate-ribofuranosyl group or 5′-phosphate-deoxyribofuranosyl group, X indicates a nitrogen atom or carbon atom, and $R_1$, $R_2$ and $R_3$ indicate each independently any of hydrogen atom, hydroxyl group, amino group, alkyl group, halogen atom, alkoxy group and mercapto group), to react with 2′,3′-dideoxycytidine, 2′,3′-dideoxyuridine or 3′-deoxythymidine in aqueous solution in the presence of phosphoric acid or phosphate through the action of microorganism of Escherichia genus, Klebsiella genus or Erwinia genus.

Further, 2′,3′-dideoxy purine nucleosides represented by the general formula [II] can be obtained by allowing purine compounds represented by a general formula [IV]

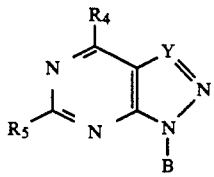

[IV]

(wherein B indicates a hydrogen atom, ribofuranosyl group, deoxyribofuranosyl group, 5′-phosphate-ribofuranosyl group or 5′-phosphate-deoxyribofuranosyl group, Y indicates a nitrogen atom or carbon atom, and $R_4$ and $R_5$ indicate each independently any of hydrogen atom, hydroxyl group, amino group, alkyl group, halogen atom, alkoxy group and mercapto group), to react with 2′,3′-dideoxycytidine, 2′,3′-dideoxyuridine or 3′-deoxythymidine in aqueous solution in the presence of phosphoric acid or phosphate through the action of microorganism of Escherichia genus, Klebsiella genus or Erwinia genus.

The purine derivatives represented by the general formula [III] and general formula [IV] can be used as they are from the constitutional ingredients of inexpensive ribonucleic acid or can be used by chemically modifying the constitutional ingredients of ribonucleic acid by well-known methods. In addition, purine base derivatives wholly synthesized, ones already commercialized or the like can also be used.

2′,3′-Dideoxycytidine, 2′,3′-dideoxyuridine and 3′-deoxythymidine can be easily obtained by known techniques.

Namely, 2′,3′-dideoxycytidine can be obtained according to the method of Horwitz et al in a way that N-benzoyl-2′-deoxy-3′, 5′- di-O-mesylcytidine derivable from 2′-deoxycytidine is refluxed with aqueous solution of sodium hydroxide in ethanol, then this is treated with dilute acetic acid, and further allowed to react with potassium tert-butoxide in dimethyl sulfoxide to obtain 2′,3′-dideoxy-2′,3′-didehydrocitidine, which is hydrogenated (J. Org. Chem., 32, 817, 1967).

Also, 2′,3′-dideoxyuridine can be obtained by hydrogenating 5′-O-benzoyl-2′-bromo-2′-deoxy-3′-O-mesyluridine derivable from uridine being a constitutional ingredient of inexpensive ribonucleic acid in the presence of palladium-barium sulfate (Chem. Pharm. Bull., 18, 554, 1970).

Moreover, 3′-deoxythymidine can be obtained in a way that, after dimesylate of thymidine is converted to 1-(2-deoxy-3,5-epoxy-β-D-threo-pentofuranosyl). thymine by the method of Horwitz et al (J. Org. Chem., 28, 942, 1963), this is allowed to react with potassium tert-butoxide in dimethylformamide and further hydrogenated catalytically (Tetrahedron Lett., 38, 2725, 1964).

As the compounds represented by said general formula [I], following compounds can be mentioned concretely.

A) Purine-9-β-D-2′,3′-dideoxyribofuranoside
B) 6-Chloropurine-9-β-D-2′,3′-dideoxyribofuranoside
C) 6-Methylpurine-9-β-D-2′,3′-dideoxyribofuranoside
D) 2-Amino-6-chloropurine- 9-β-D-2′,3′-dideoxyribofuranoside
E) 2-Amino-6-methylpurine-9-β-D-2′,3′-dideoxyribofuranoside
F) 2,6-Diaminopurine-9-β-D-2′,3′-dideoxyribofuranoside
G) 2,6-Dihydroxypurine-9-β-D-2′,3′-dideoxyribofuranoside
H) 2,6-Dichloropurine-9-β-D-2′,3′-dideoxyribofuranoside
I) 6-Mercaptopurine-9-β-D-2′,3′-dideoxyribofuranoside
J) 2-Amino-6-mercaptopurine-9-β-D-2′,3′-dideoxyribofuranoside Moreover, as the compounds represented by said general formula [II], following compounds can be mentioned concretely.

K) 6-Hydroxy-7-deaza-8-azapurine-9-β-D-2′,3′-dideoxyribofuranoside
L) 6-Amino-8-azapurine-9-β-D-2′,3′-dideoxyribofuranoside As the methods to obtain 2′,3′-dideoxy purine nucleoside from the raw material of 2′,3′-dideoxy pyrimidine nucleoside using the base-exchange reaction by microorganism or enzyme, there are two reports shown below.

The first report deals with a method to obtain 2′,3′-dideoxyadenosine, 2′,3′-dideoxyinosine and 2′,3′-dideoxyguanosine using Escherichia coli AJ-2595 (Nucleic Acids Symposium Series, No. 20, 17, 1988).

In this report, however, the identification of products is made only by HPLC and the scale is no larger than that in laboratory as proved by the reaction liquor of 5 ml. And yet, the isolation and purification methods being necessary for the industrial production are not touched on at all, the practical isolation being not conducted. Furthermore, the yield calculated from the value of HPLC is low (33 % at a concentration of 50 mM in the case of synthesis of 2′,3′-dideoxyadenosine), the reaction time needed is as long as 24 hours, and so on. Thus, this is hard to say to be an industrial technique also in these points.

The second report is concerned with the synthesis of 2′,3′-dideoxy nucleosides such as 6-N-piperidinopurine-9-β-D-2′,3′-dideoxyribofuranoside using purified thymidine phosphorylase and purine nucleoside phosphorylase (Japanese Unexamined Patent Publication No. Sho 63-267796).

This report is difficult however to be regarded as an industrial production method for obtaining the product in better yield during short time because of use of two enzymes being expensive and hard to obtain, low yield, very long reaction time from several days to around a week, and others.

The invention provides new industrial synthetic process having been found for the first time as a result of extensive investigations in fine detail of technique for overcoming the respective drawbacks as can be seen in the reports above and is characterized in that 2',3'-dideoxy purine nucleosides are given in good yield during short time.

In other words, the process of the invention is more excellent than conventional ones in several points shown below.

The first point lies in the use of *Escherichia coli*, *Klebsiella pneumoniae* and *Erwinia herbicola* as the microorganisms for the reactions in the invention; particularly in the fact that, among them, *E. coli* JA-300 strain, *K. pneumoniae* IFO-3321 strain and *E. herbicola* IFO-12686 strain have been found to have a high base-exchangeability. The microorganisms used in the present reaction, in particular, *E. coli* JA-300 strain, *K. pneumoniae* IFO-3321 strain and *E. herbicola* IFO-12686 strain are ones obtained through scrupulous screening over a wide range making it possible to obtain 2',3'-dideoxy purine nucleosides in good yield from 2',3'-dideoxy pyrimidine nucleoside and purine derivatives.

The microorganisms used for the reaction in the invention are living fungi and can be cultured proliferously for use by selecting appropriate culture conditions resulting in lower cost than the case of using purified enzymes.

The second point lies in having found the conditions to obtain good yield during short time by examining minutely the reaction conditions such as reaction temperature, pH of reaction liquor and change of reaction overtime.

Namely a reaction temperature of 45° to 55° C. has been found to be most suitable. This is a sufficient reaction temperature for pyrimidine nucleoside phosphorylase and purine nucleoside phosphorylase being necessary for the reaction used in the invention to exhibit the activity and yet necessary and sufficient temperature to suppress the working of enzymes such as deaminase being not directly necessary for the reaction.

A matter to take care when performing the reaction at this reaction temperature (45°-55° C.) is that the temperature of 45° to 55° C. must be retained already from the start of reaction.

Saying concretely, a reaction liquid suspended the reaction substarte (2',3'-dideoxy pyrimidine nucleoside and purine nucleoside derivative) and a liquid suspended the fungus bodies are each independently retained at 45° to 55° C. and then both are mixed to start the reaction.

If the temperature of liquid suspended the substrate differs from that of liquid containing the fungus bodies at the time of starting the reaction, the temperature on starting of reaction by mixing both would not become appropriate temperature (45°-55° C.) to be connected with a decrease in reaction yield.

Moreover, it has also been found from the investigation that pH is most suitable to be 7.5 to 9.0 from the points of reaction velocity of reaction liquor and the stability of product.

Furthermore, in the case of the reaction system used for the present reaction, the fact that the reaction time is sufficient to be several hours has been found from the comparison of minute changes in yield over the time.

The third point lies in the establishment of simple isolation and purification methods. Concretely, this consists of centrifugal separation procedure of reaction liquor and purification means with adsorptive resin.

Namely, the reaction liquor after the completion of reaction is submitted to centrifugal separation to precipitate the fungus bodies and the supernatant thereof is collected separately by the decantation method. The supernatant thus obtained is passed through a column packed with adsorptive resin to adsorb only the product and to eliminate phosphate etc. After the column is washed well with water, adsorbed product is eluted with suitable organic solvent to obtain 2',3'-dideoxy purine nucleosides. Such method has been found by us.

Based on the three points as described above, 2',3'-dideoxy purine nucleosides can be obtained with simple procedure in good yield during short time.

2',3'-dideoxy purine nucleosides of the invention are useful as antiviral agents and antiretroviral agents, in particular, as anti-HIV agents and effective as preventive drugs and therapeutic drugs for acquired immunodeficiency syndrome (AIDS).

Moreover, 2',3'-dideoxy purine nucleosides of the invention have the property as a DNA chain terminator and are useful medicines in the genetic engineering.

EXAMPLE 1

In a fermenter jar were placed 10 L of liquid medium containing 5 g/L of yeast extract, 10 g/L of peptone and 5 g/L of NaCl and being adjusted to pH 7.0, which were pasteurized.

To this medium were inoculated 100 mg of *E. coli* JA-300 (Gene., 10, 157 (1980)), which were cultured under shaking for 16 hours at 37° C.

The fungus bodies were collected from the medium by centrifugal separation and, after washed with physiological saline, these were suspended into 0.05M phosphate buffer (pH 7.5) adjusted with $KH_2PO_4$ and $Na_2HPO_4$ (100 mg wet/mL).

After warmed to 50° C., 70 ml of said suspension of fungus bodies were added to 70 ml of reaction liquor which consisted of 0.05M phosphate buffer containing 7.0 mmol of 2',3'-dideoxyuridine and 7.0 mmol of purine and being adjusted to pH 7.5 with $KH_2PO_4$ and $Na_2HPO_4$ and which were warmed beforehand to 50° C.

This was shaken while retaining at 50° C. for 4 hours and then heated at 100° C. for 3 minutes.

After the temperature of reaction, the fungus bodies were allowed to precipitate by centrifugal separation and the remaining supernatant was transferred to a beaker by the decantation method (supernatant 1).

To the fungus bodies being precipitated were added 70 ml of phosphate buffer (0.05M) with pH 7.5. After stirred for some time, centrifugal separation procedure was carried out and the supernatant was transferred to a beaker by the decantation method. This procedure was repeated twice (supernatants 2 and 3).

Said supernatants 1,2 and 3 were passed in sequence through a column (4×20 cm) packed with adsorptive resin (HP-20, made by Mitsubishi Kasei).

After the application of samples, this column was washed with 1 L of distilled water and the product was eluted with methanol.

After eliminated the solvent, the product was dissolved again into chloroform containing 10% methanol, which was submitted to chromatography using a column (4×20 cm) packed with silica gel. For the mobile layer, chloroform containing 10% methanol was used.

The fractions containing the product were combined and concentrated, and the solids obtained were recrystlized from methanol. The crystals were dried to obtain purine-9-β-D-2',3-dideoxy-ribofuranoside (0.6629 g, 3.01 mmol) (yield: 43%).

Melting point: 152° C.

Figures 1, 2:
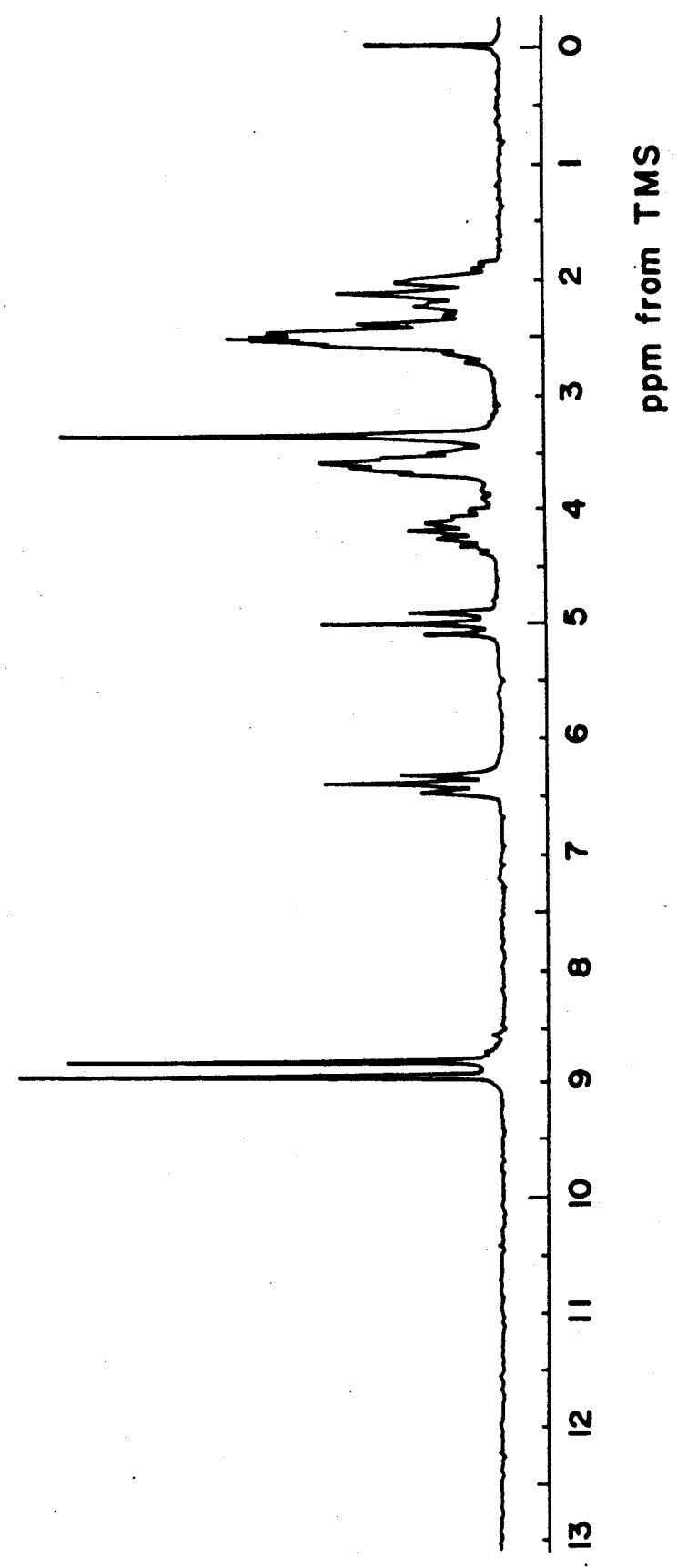
Figure 2:
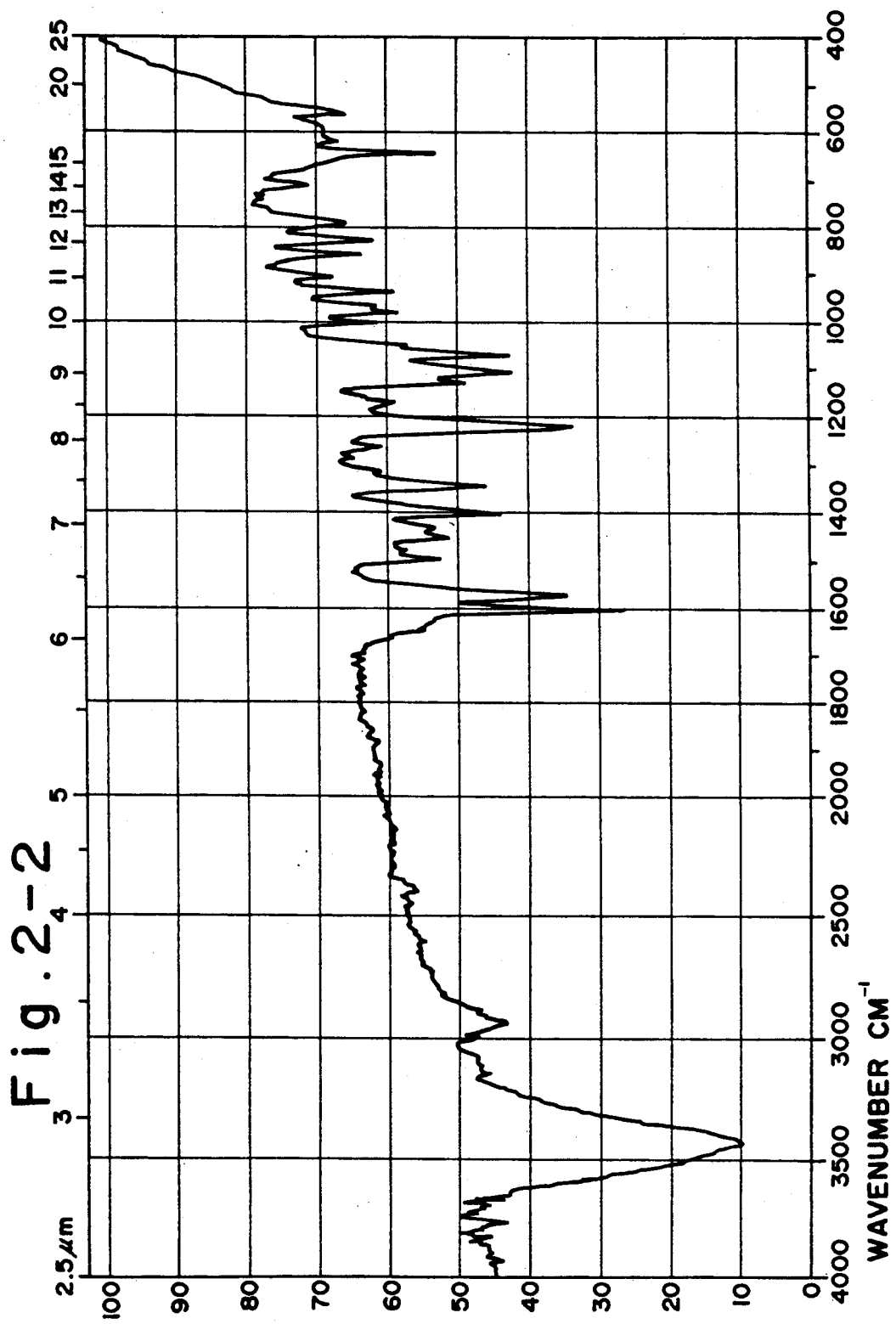

1H NMR (DMSO d6) and IR (KBr) are shown in FIG. 1-1 and FIG. 1-2, respectively.

EXAMPLE 2

Similar reaction was conducted using purine-9-β-D-2'-deoxy-ribofuranoside in place of purine in Example 1. The product obtained through the reaction was post-treated and purified by the methods shown in Example 1 to obtain purine-9-β-D-2',3'-dideoxy-ribofuranoside (0.3237 g, 1.47 mmol) (yield: 21%) as dry solids.

EXAMPLE 3

Similar reaction was conducted using purine-9-β-D-2'-deoxy-ribofuranoside in place of purine in Example 1. The product obtained through the reaction was post-treated and purified by the methods shown in Example 1 to obtain purine-9-β-D-2',3'-dideoxyribofuranoside (0.4162 g, 1.89 mmol) (yield: 27%) as dry solids.

EXAMPLE 4

Similar reaction was conducted using 3'-deoxythymidine in place of 2',3'-dideoxyuridine in Example 1. The product obtained through the reaction was post-treated and purified by the methods shown in Example 1 to obtain purine-9-β-D-2',3'-dideoxyribofuranoside (0.6276 g, 2.85 mmol) (yield: 41%) as dry solids.

EXAMPLE 5

Similar reaction was conducted using 2',3'-dideoxycytidine in place of 2',3'-dideoxyuridine in Example 1. The product obtained through the reaction was post-treated and purified by the methods shown in Example 1 to obtain purine-9-β-D-2',3'-dideoxyribofuranoside (0.1850 g, 0.84 mmol) (yield: 12%) as dry solids.

EXAMPLE 6

Similar reaction was conducted using 6-chloropurine in place of purine in Example 1. The product obtained through the reaction was post-treated and purified by the methods shown in Example 1 to obtain 6-chloropurine-9-β-D-2',3'-dideoxyribofuranoside (0.9267 g, 3.64 mmol) (yield: 52%) as dry solids. Melting point: 104° C. 1H NMR (DMSO d6) and IR (KBr) are shown in FIG. 2-1 and FIG. 2-2, respectively.

EXAMPLE 7

Similar reaction was conducted using 6-chloropurine-9-β-D-ribofuranoside in place of purine in Example 1. The product obtained through the reaction was post-treated and purified by the methods shown in Example 1 to obtain 6-chloropurine-9-β-D-2',3'-dideoxyribofuranoside (0.6951 g, 2.73 mmol) (yield: 39%) as dry solids.

EXAMPLE 8

Figures 1, 3:
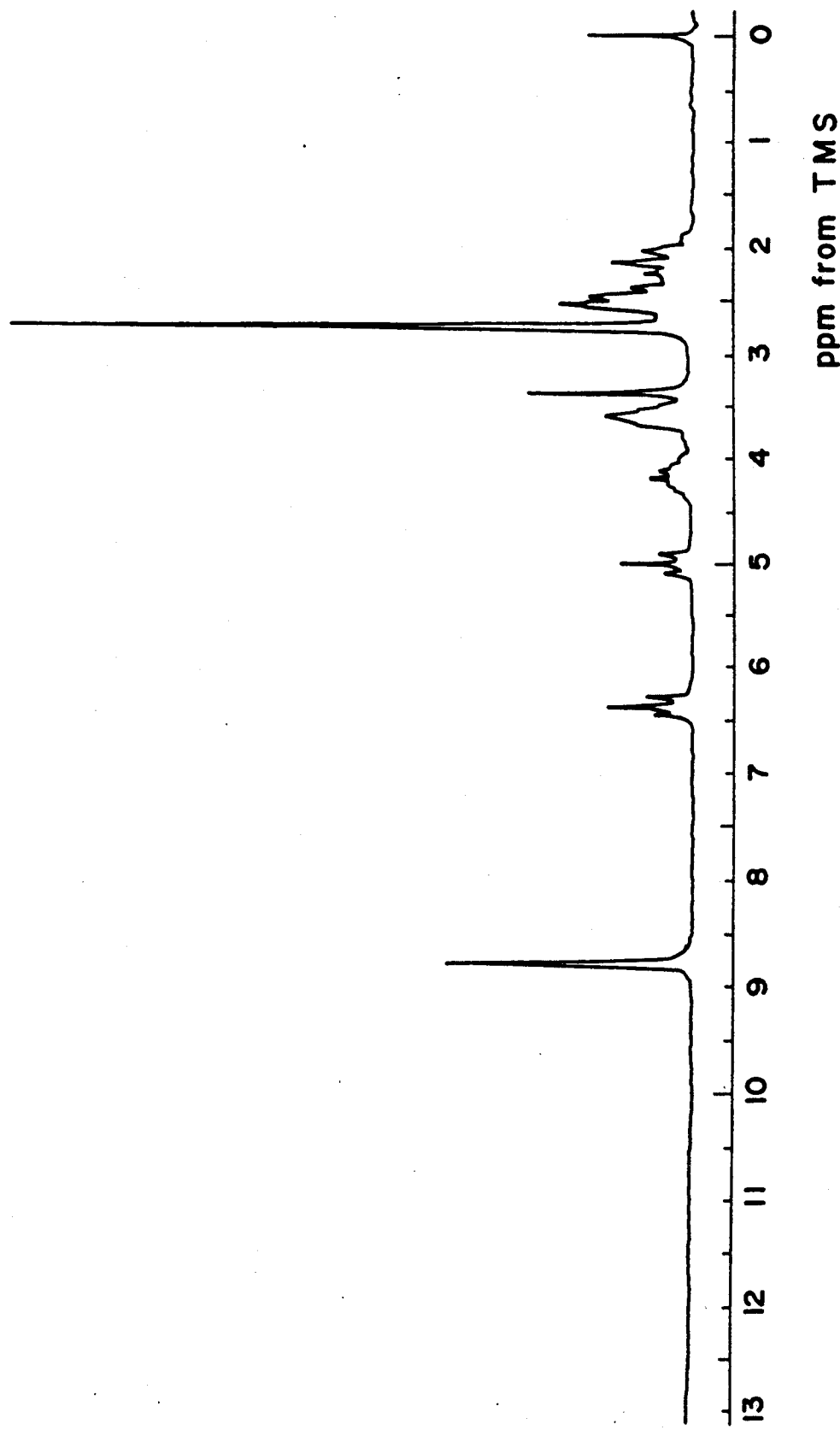
Figures 2, 3:
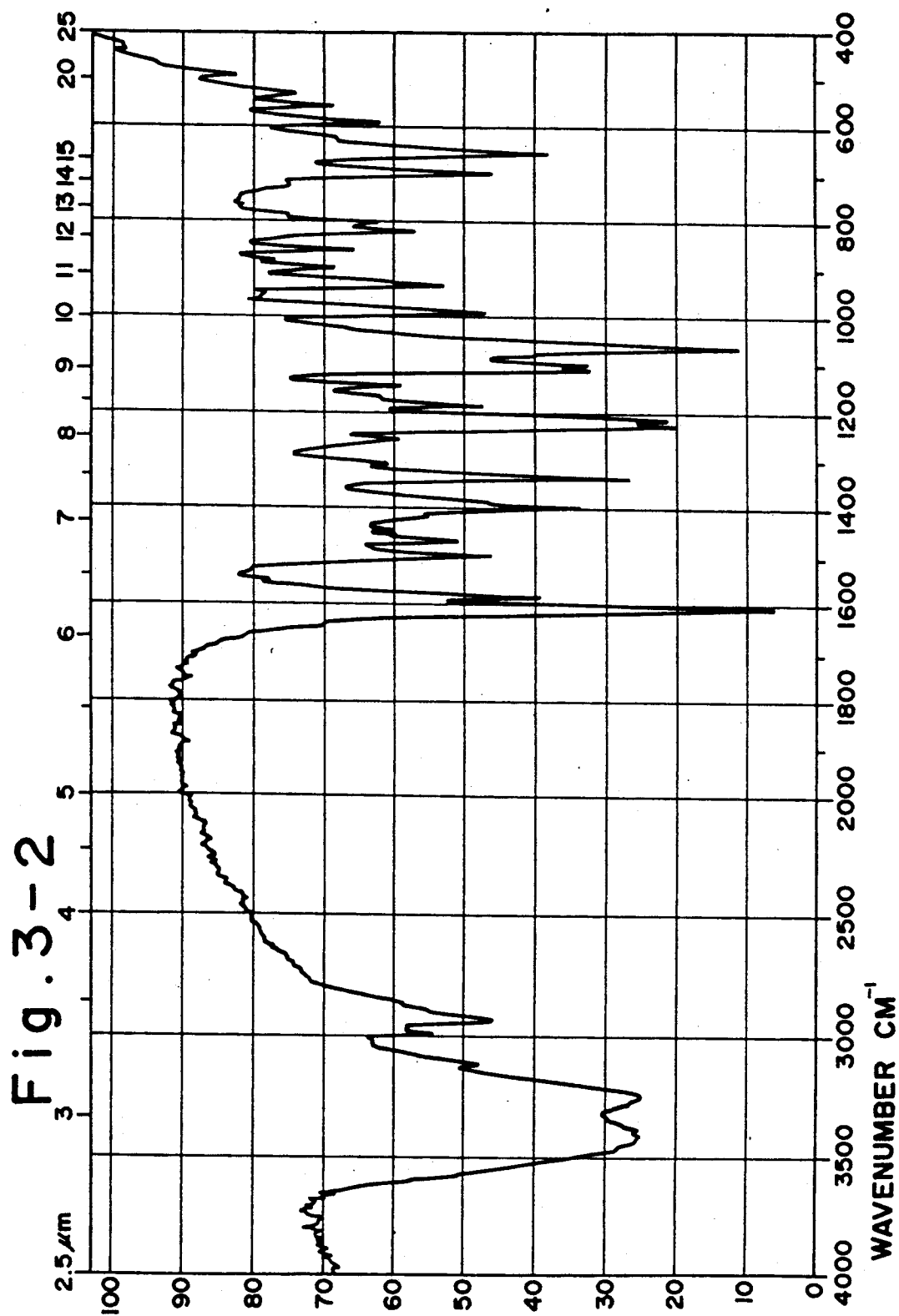

Similar reaction was conducted using 6-methylpurine in place of purine in Example 1. The product obtained through the reaction was post-treated and purified by the methods shown in Example 1 to obtain 6-methylpurine-9-β-D-2',3'-dideoxyribofuranoside (0.9019 g, 3.85 mmol) (yield: 55%) as dry solids. Melting point: 110° C. 1H NMR (DMSO d6) and IR (KBr) are shown in FIG. 3-1 and FIG. 3-2, respectively.

EXAMPLE 9

Similar reaction was conducted using 6-methylpurine-9-β-D-ribofuranoside in place of purine in Example 1. The product obtained through the reaction was post-treated and purified by the methods shown in Example 1 to obtain 6-methylpurine-9-β-D-2',3'-dideoxyribofuranoside (0.5247 g, 2.24 mmol) (yield: 32%) as dry solids.

EXAMPLE 10

Similar reaction was conducted using 2-amino-6-chloropurine in place of purine in Example 1. The product obtained through the reaction was post-treated and purified by the methods shown in Example 1 to obtain 2-amino-6-chloropurine-9-β-D-2',3'-dideoxyribofuranoside (1.057 g, 3.92 mmol) (yield: 56%) as dry solids.

Melting point: 138° C.

Figures 1, 4:
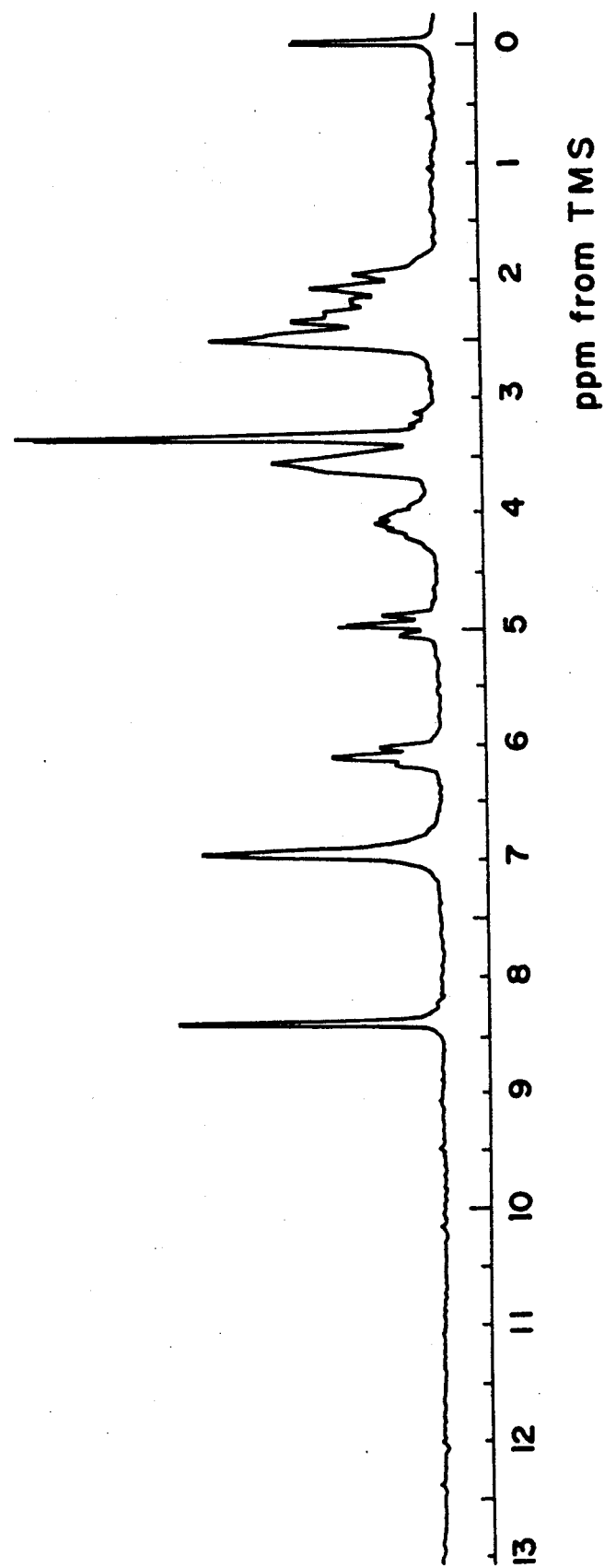
Figures 2, 4:
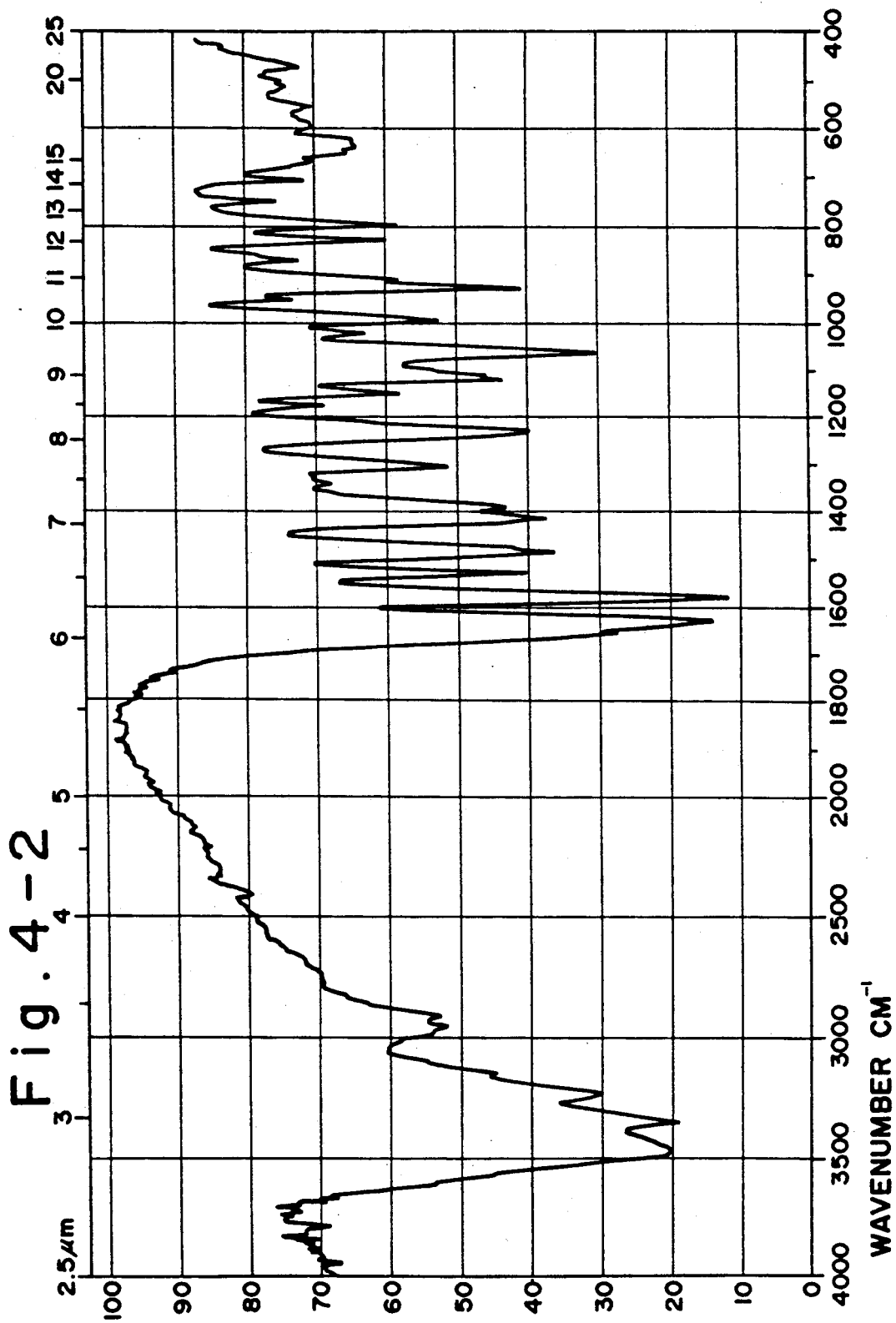

1H NMR (DMSO d6) and IR (KBr) are shown in FIG. 4-1 and FIG. 4-2, respectively.

EXAMPLE 11

Similar reaction was conducted except that 6-mercaptopurine was used in place of purine in Example 1 and further pH of the reaction liquor was made to be 9. The reason why pH was made to be 9 is for raising the solubility of 6-mercaptopurine being the medium.

The product obtained through the reaction was post-treated and purified by the methods shown in Example 1 to obtain 6-mercapto-purine-9-β-D-2',3'-dideoxyribofuranoside (0.2119 g, 0.84 mmol) (yield: 12%) as dry solids.

Melting point: 188° C.

Figures 1, 5:
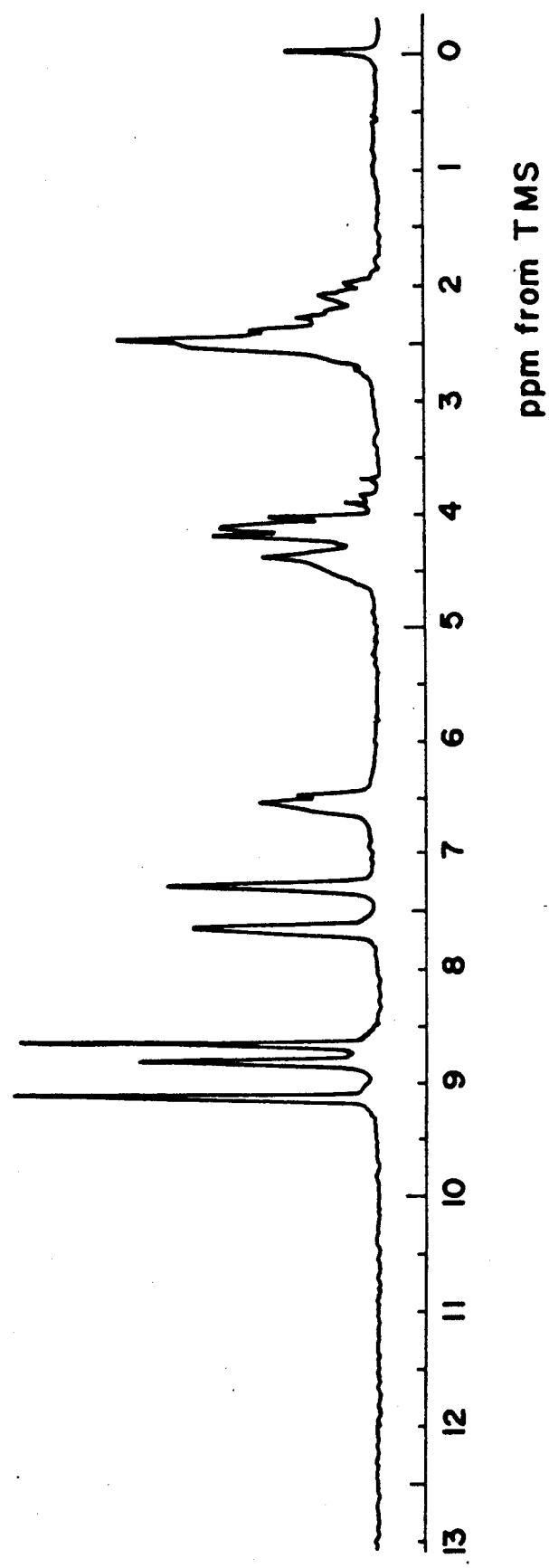
Figures 2, 5:
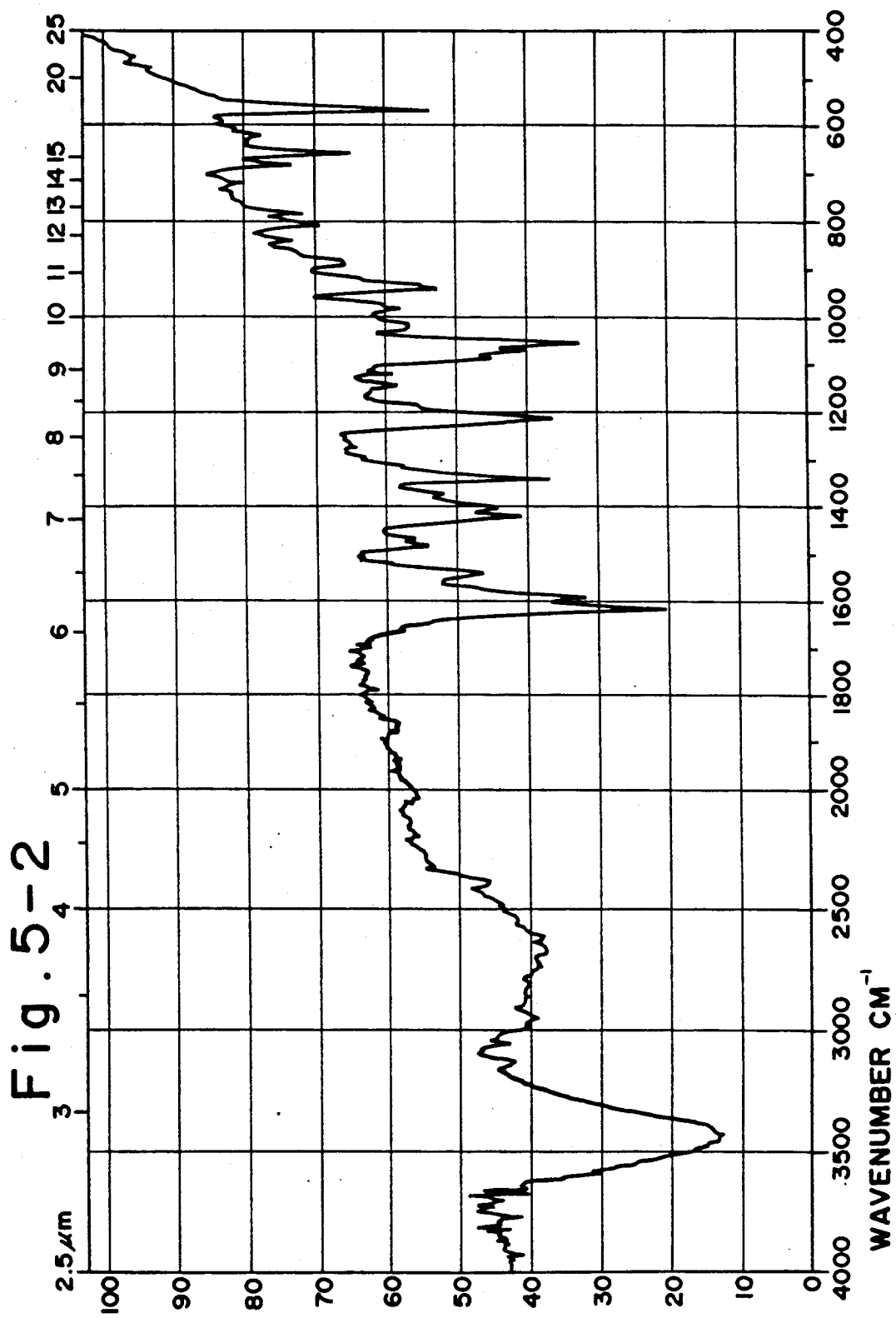

1H NMR (pyridine d5) and IR (KBr) are shown in FIG. 5-1 and FIG. 5-2, respectively.

EXAMPLE 12

Similar reaction was conducted using 6-mercaptopurine-9-β-D-ribofuranoside in place of purine in Example 1. The product obtained through the reaction was post-treated and purified by the methods shown in Example 1 to obtain 6-mercaptopurine-9-β-D-2',3'-dideoxyribofuranoside (0.3709 g, 1.47 mmol) (yield: 21%) as dry solids.

EXAMPLE 13

Similar reaction was conducted using 6-mercaptopurine-9-β-D-ribofuranoside-5'-monophosphate in place of purine in Example 1. The product obtained through the reaction was post-treated and purified by the methods shown in Example 1 to obtain 6-mercaptopurine-9-β-D-2',3'-dideoxyribofuranoside (0.3179 g, 1.26 mmol) (yield: 18%) as dry solids.

EXAMPLE 14

Similar reaction was conducted except that 2-amino-6-mercaptopurine was used in place of purine in Example 1 and further pH of the reaction liquor was made to be 9. The reason why pH was made to be 9 is for raising the solubility of 2-amino-6-mercaptopurine being the raw material.

The product obtained through the reaction was post-treated and purified by the methods shown in Example 1 to obtain 2-amino-6-mercaptopurine-9-β-D-2',3'-dideoxyribofuranoside (0.3181 g, 1.19 mmol) (yield: 17%) as dry solids.

Melting point: 203° C.

Figures 1, 6:
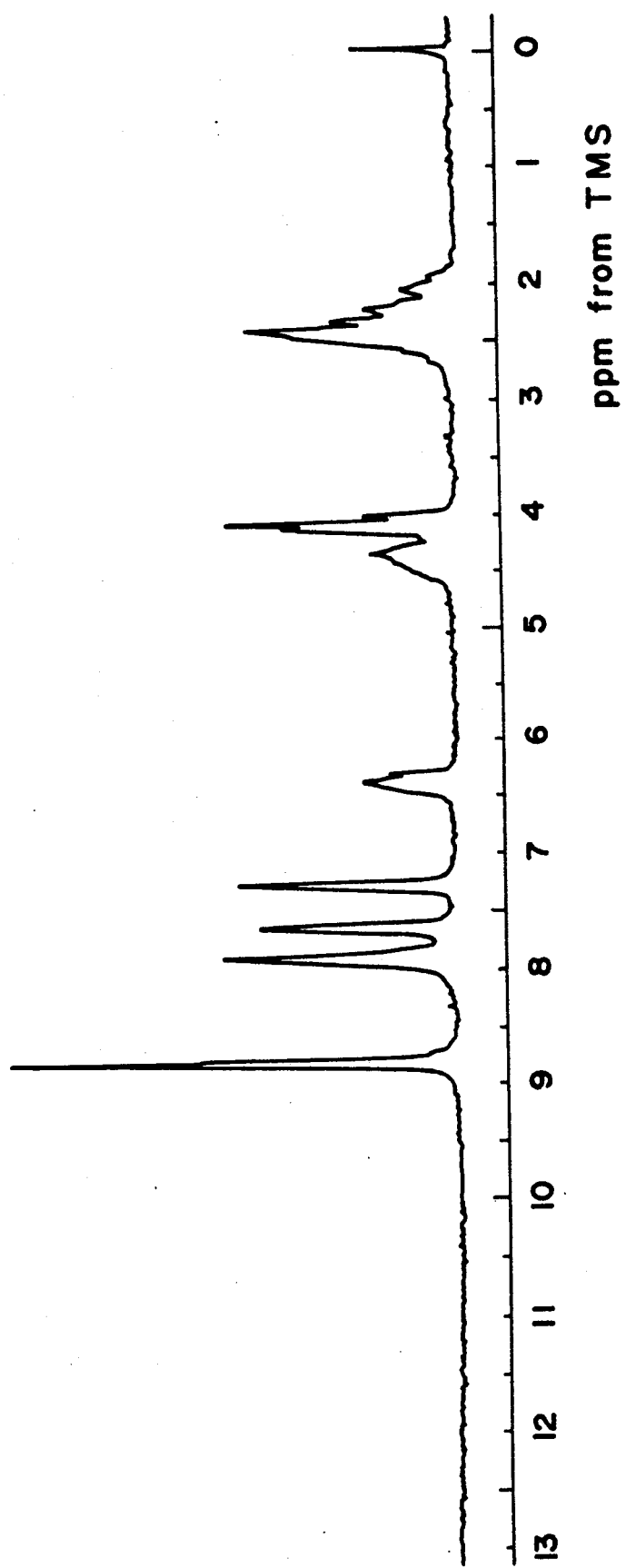

1H NMR (pyridine d5) and IR (KBr) are shown in FIG. 6-1 and FIG. 6-2, respectively.

EXAMPLE 15

Similar reaction was conducted using 2-amino-6-mercaptopurine- 9-β-D-ribofuranoside in place of purine in Example 1. The product obtained through the reaction was post-treated and purified by the methods shown in Example 1 to obtain 2-amino-6-mercaptopurine-9-β-D-2',3'-dideoxyribofuranoside (0.4304 g, 1.61 mmol) (yield: 23%) as dry solids.

EXAMPLE 16

Figures 1, 7:
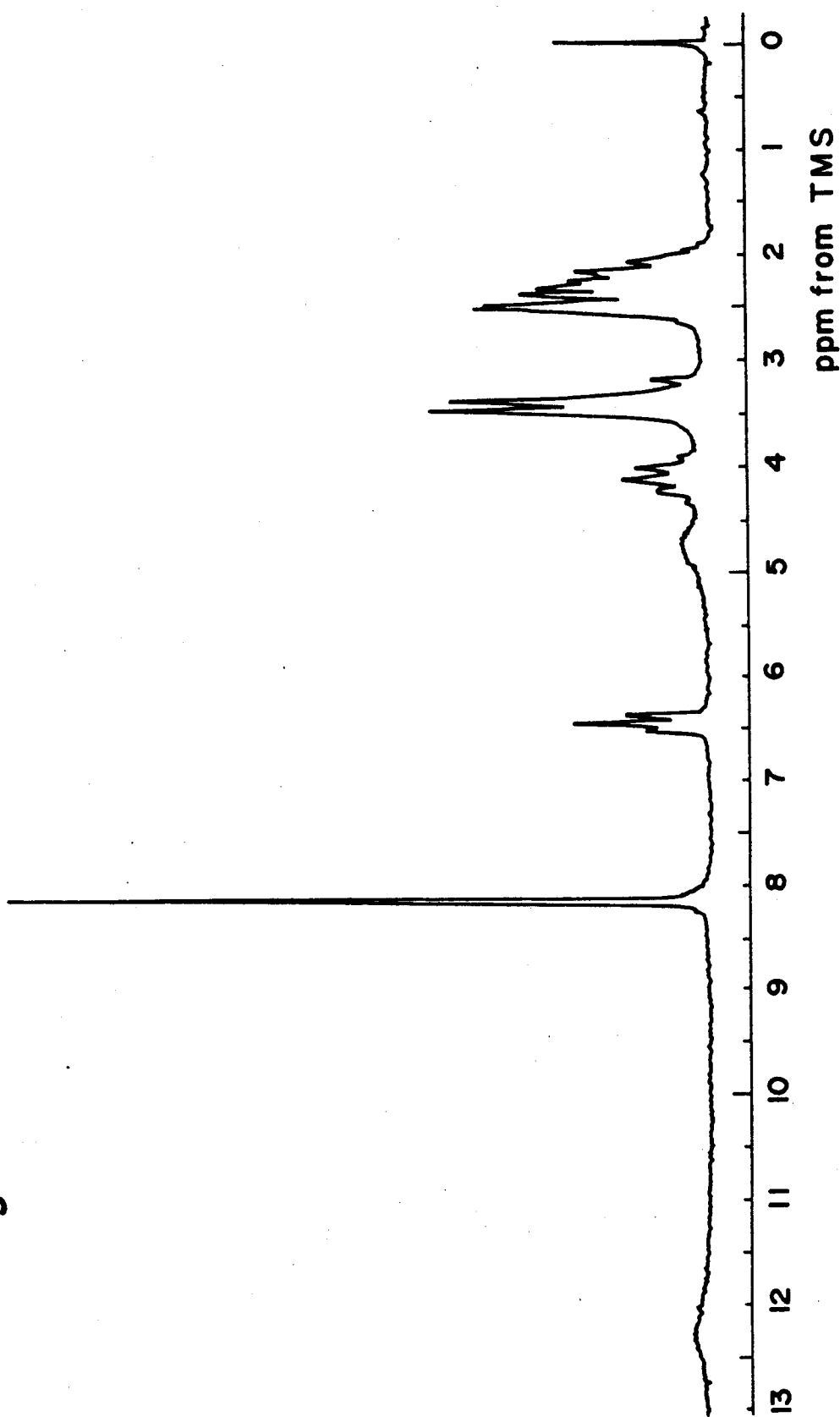

Similar reaction was conducted using 6-hydroxy-7deaza-8-azapurine in place of purine in Example 1. The product obtained through the reaction was post-treated and purified by the methods shown in Example 1 obtain 6-hydroxy-7-deaza-8-azapurine-9-β-D-2',3'-dideoxyribofuranoside (0.6780 g, 2.87 mmol) (yield: 41%) as dry solids. Melting point: 184° C. 1H NMR (DMSO d6) and IR (KBr) are shown in FIG. 7-1 and FIG. 7-2, respectively.

EXAMPLE 17

Similar reaction was conducted using 3-deoxythymidine in place of 2',3'-dideoxyuridine in Example 1. The product obtained through the reaction was post-treated and purified by the methods shown in Example 1 obtain 6-hydroxy-7-deaza-8-azapurine-9-β-D-2',3'-dideoxyribofuranoside (0.5953 g, 2.52 mmol) (yield: 36%) as dry solids.

EXAMPLE 18

Similar reaction was conducted using 6-amino-8-azapurine in place of purine in Example 1. The product obtained through the reaction was post-treated and purified by the methods shown in Example 1 to obtain 6-amino-8-azapurine-9-β-D-2',3'-dideoxyribofuranoside (0.8599 g, 3.64 mmol) (yield: 52%) as dry solids. Melting point: 192° C.

Figures 1, 8:
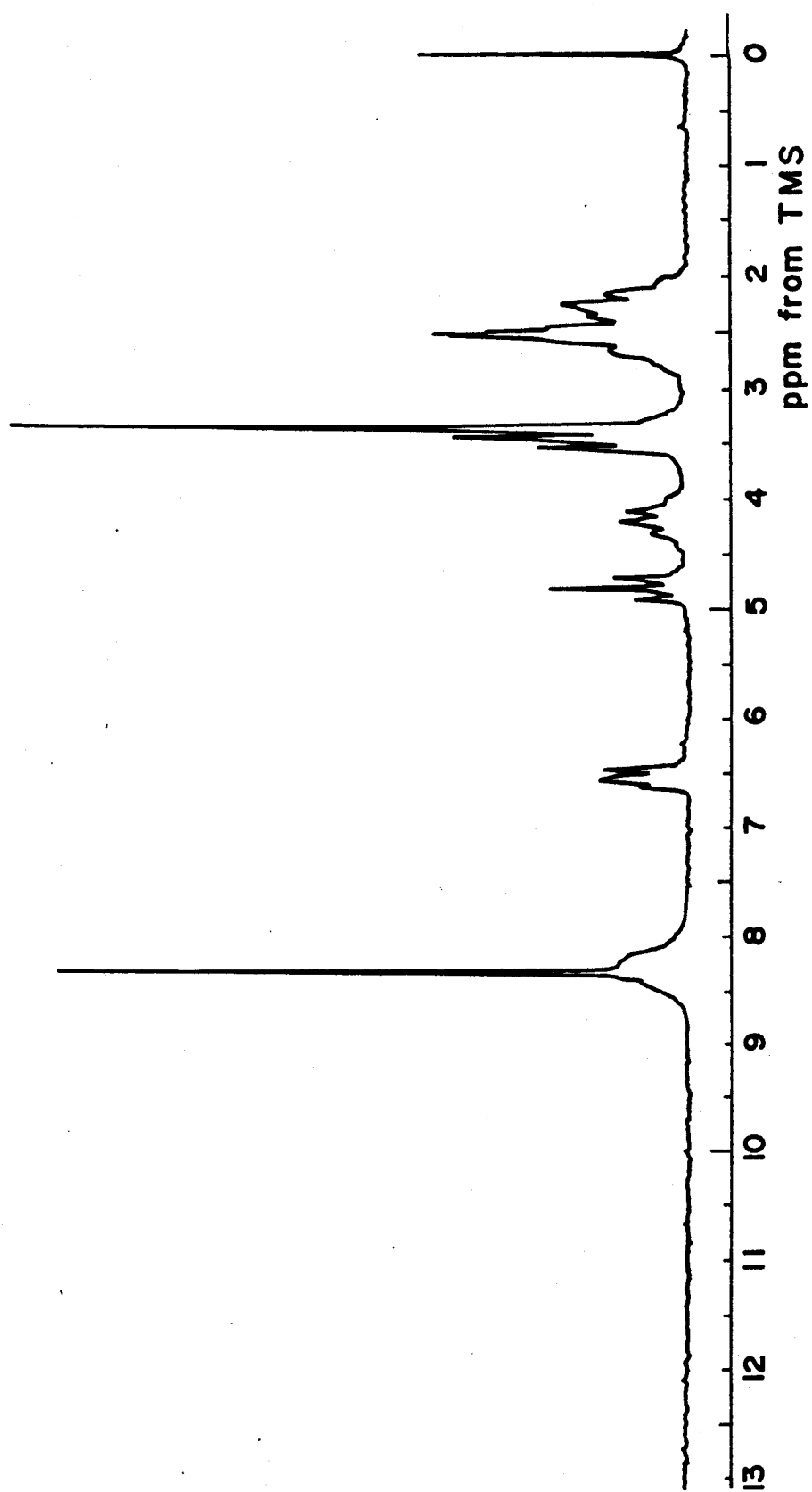
Figures 2, 8:
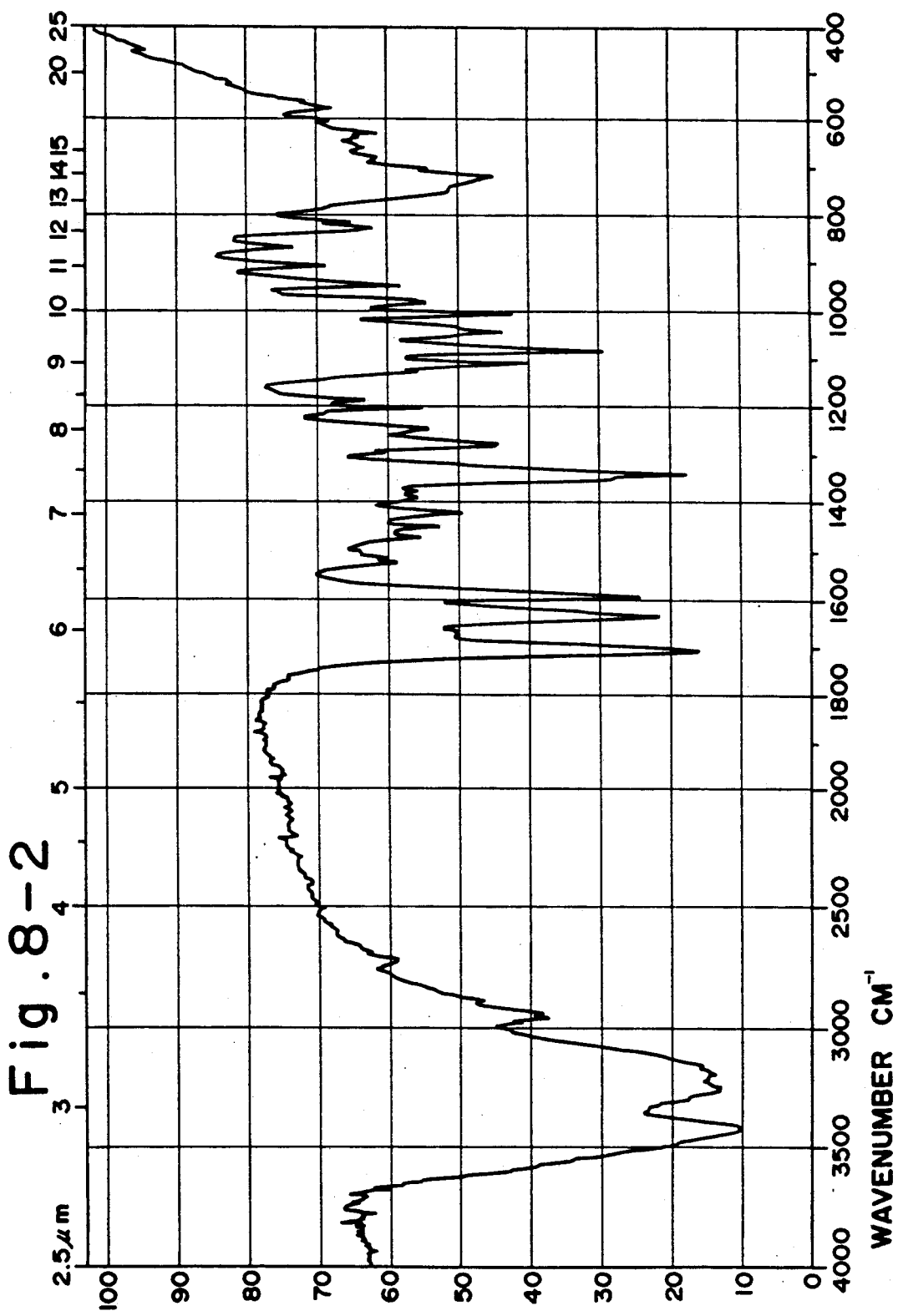

1H NMR (DMSO d6) and IR (KBr) are shown in FIG. 8-1 and FIG. 8-2, respectively.

EXAMPLE 19

Similar reaction was conducted using E. coli JC-411 (Proc. Nat. Acad. Sci. U.S.A. 60,160 (1968)) in place of E. coli JA-300 in Example 1.

The product obtained through the reaction was post-treated and purified by the methods shown in Example 1 to obtain purine-9-β-D-2',3'-dideoxyribofuranoside (0.4780 g, 2.17 mmol) (yield: 31%) as dry solids.

EXAMPLE 20

Similar reaction was conducted using K. pneumoniae IFO-3321 (described in List of Cultures, 1984, published by Institute of Fermentation, Foundation) in place of E. coli JA-300 in Example 10.

The product obtained through the reaction was post-treated and purified by the methods shown in Example 1 to obtain 2-amino-6-chloropurine-9-β-D-2',3'-dideoxyribofuranoside (1.019 g, 3.78 mmol) (yield: 54%) as dry solids.

EXAMPLE 21

Similar reaction was conducted using E. herbicola IFO-12686 (described in List of Cultures, 1984, published by Institute of Fermentation, Foundation) in place of E. coli JA-300 in Example 8.

The product obtained through the reaction was post-treated and purified by the methods shown in Example 1 to obtain 6-methyl- purine-9-β-D-2',3'-dideoxyribofuranoside (0.6395 g, 2.73 mmol) (yield: 39%) as dry solids.

Example 22

Similar reaction was conducted using K. pneumoniae IFO-3321 (described in List of Cultures, 1984, published by Institute of Fermentation, Foundation) in place of E. coli JA-300 in Example 11.

The product obtained through the reaction was post-treated and purified by the methods shown in Example 1 to obtain 6-mercapto- purine-9-β-D-2',3'-dideoxyribofuranoside (0.2649 g, 1.05 mmol) (yield: 15%) as dry solids.

As described above, the novel 2',3'-dideoxy purine nucleosides of the invention exert the effects as antiviral agents and anti-retroviral agents and, in particular, are useful as anti-HIV agents. They are thus useful as preventive drugs and therapeutic drugs for AIDS. Moreover, from the property as a DNA chain terminator, they can also be used as reagents in the genetic engineering.

The novel 2',3'-dideoxy purine nucleosides of the invention can be used each independently and also in a combined form mixing two or more compounds or in a form of using together. In addition, they are excellent substances making it possible to lower the dosage thereof by using them together with conventional 2',3'-dideoxy nucleosides (DDC, DDA, DDI, AZT, etc.) resulting in the alleviation of side effects.

Furthermore, in accordance with the preparing processes of the invention, 2',3'-dideoxy purine nucleosides can be isolated from 2',3'-dideoxy pyrimidine nucleoside and purine derivatives during short reaction time, in good yield and easily. Yet, the reagents to be used are also inexpensive and the microorganisms to be used are also possible to be cultured proliferously with simple culture system. Further, with respect to the reaction equipment, too, such a culture equipment that is generally placed on the market can be directly used and special equipment is not needed. From these and other reasons, they are excellent preparing processes being economical and possible to put into practice industrially.

What is claimed is:

1. The compound 2-Amino-6-chloropurine-9-β-D-2',3'-dideoxyribofuranoside.

* * * * *

UNITED STATES PATENT AND TRADEMARK OFFICE
CERTIFICATE OF CORRECTION

PATENT NO. : 5,053,499
DATED : October 1, 1991
INVENTOR(S) : Eiji Kojima, et al

It is certified that error appears in the above-indentified patent and that said Letters Patent is hereby corrected as shown below:

Column 1, line 54, delete "3'-azidethymidine", insert --3'-azidothymidine--.

Column 2, line 4, delete "DA", insert --DDA--.

Column 4, line 1, delete "didehydrocitidine", insert --didehydrocytidine--
line 11, delete "pentofuranosyl). thy-", insert --pentofuranosyl)-thy- --.

Column 9, line 32, delete "Example 1", insert --Example 16--.

Signed and Sealed this

Eighteenth Day of January, 1994

Attest:

BRUCE LEHMAN

Attesting Officer      Commissioner of Patents and Trademarks